US00PP09934P

United States Patent [19]

Fuess

[11] Patent Number: Plant 9,934

[45] Date of Patent: Jun. 24, 1997

[54] CHRYSANTHEMUM PLANT NAMED 'EMPIRE SCOTTSDALE'

[76] Inventor: Janet S. Fuess, 22 Country Club Dr., New York Mills, N.Y. 13417

[21] Appl. No.: 670,276

[22] Filed: Jun. 13, 1996

[51] Int. Cl.[6] ..... A01H 5/00

[52] U.S. Cl. ..... Plt./79

[58] Field of Search ..... Plt./79, 78, 76

[56] References Cited

U.S. PATENT DOCUMENTS

P.P. 7,993 9/1992 Hesse ..... Plt./79

*Primary Examiner*—Howard J. Locker

*Attorney, Agent, or Firm*—Foley & Lardner

[57] ABSTRACT

A new and distinct cultivar of Chrysanthemum plant named Empire Scottsdale, characterized particularly by its bronze ray florets, fully double flowers with no disc florets; compact, cushion habit, making it suitable for greenhouse or garden culture; 4.5–5.0 cm capitulum diameter; a natural season flower date of September 25 in New Hartford, N.Y., and its eight week flower response in light/shade programs.

1 Drawing Sheet

The present invention comprises a new and distinct cultivar of Chrysanthemum, botanically known as *Dendranthema grandiflora,* and referred to by the cultivar name Empire Scottsdale.

Empire Scottsdale is a product of a planned breeding program which had the objective of creating new chrysanthemum cultivars with a freely branching compact cushion habit, early flower response, bronze decorative flowers and adaptability as a garden variety. Such traits in combination were not present in previously available commercial cultivars.

Empire Scottsdale was originated from a hybridization made by the inventor in a controlled breeding program in New Hartford, N.Y. in 1991. The female parent was Empire Cheyenne, an orange-bronze decorative disclosed in U.S. Plant Pat. No. 8,973. The male parent of Empire Scottsdale was a yellow-bronze decorative identified as C89-14, a proprietary breeding line.

Empire Scottsdale was discovered and selected as one flowering plant within the progeny of the stated parentage by the inventor in August 1992 in a controlled environment in New Hartford, N.Y.

The first act of asexual reproduction of Empire Scottsdale was accomplished when vegetative cuttings were taken from the initial selection in October 1992 in a controlled environment in New Hartford, N.Y. by a technician working under formulations established and supervised by the inventor. Horticultural examination of selected units initiated in August 1993 has demonstrated that the combination of characteristics as herein disclosed for Empire Scottsdale are firmly fixed and are retained through successive generations of asexual reproduction.

Empire Scottsdale has not been observed under all possible environmental conditions. The phenotype may vary significantly with variations in environment such as temperature, light intensity, and day length, without, however, any variation in genotype. The following observations, measurements and comparisons describe plants grown in New Hartford, N.Y. under natural outdoor conditions which approximate those generally used in commercial practice.

The following traits have been repeatedly observed and are determined to be basic characteristics of Empire Scottsdale, which in combination distinguish this Chrysanthemum as a new and distinct cultivar:

1. Bronze ray florets.
2. Fully double flowers with no disc florets.

3. Fully expanded ray florets are approximately 2.3 cm long and 0.8 cm wide, with regular dentate tips.
4. Average of 296 ray florets per flower.
5. Capitulum is 4.5–5.0 cm in diameter.
6. Eight (8) week flower response in light/shade programs.
7. Performs well in the outdoor garden, flowering approximately September 25 in New Hartford, N.Y.
8. Compact cushion habit, making it suitable for production in 4" to 8" containers.

Of the many commercial cultivars known to the present inventor, the most similar in comparison to Empire Scottsdale is the female parent Empire Cheyenne. In comparison to Empire Cheyenne, Empire Scottsdale flowers approximately 1 week later, both in natural season and light/shade programs, has a softer, true decorative texture rather than button-like, is slightly more compact, and has a lighter bronze ray floret color. The capitulum size, fully double flowers, and adaptability to greenhouse or garden cultures are similar to those same characteristics of Empire Cheyenne.

The accompanying photographic drawing comprises a perspective view showing typical inflorescence and foliage characteristics of Empire Scottsdale, with colors being as nearly true as possible with illustrations of this type.

In the following description, color references are made to The Royal Horticultural Society Colour Chart. The color values were determined between 10:00 AM and 1:00 PM on Sep. 29, 1995 under 4,000 footcandles at New Hartford, N.Y.

Classification:

*Botanical.*—*Dendranthema grandiflora* cv. Empire Scottsdale.

*Commercial.*—Decorative garden mum.

INFLORESENCE

A. Capitulum:

*Form.*—Decorative.

*Type.*—Double.

*Diameter across face.*—4.5 to 5.0 cm.

B. Corolla of ray florets:

*Color (General tonality from a distance of three meters).*—Bronze.

*Color* (*upper surface*).—Center is 22A, outwardly toward edge color is 22B.

*Color* (*lower surface*).—22C.

C. Corolla of disc florets: No disc florets.

D. Reproductive organs:

*Androecium.*—None.

*Gynoecium.*—Present on ray florets; style 0.4 cm, biburcated.

II. PLANT

A. General appearance:

*Height.*—23–26 cm, when grown in an 8" pot.

B. Foliage:

*Color* (*lower surface*).—137D.

*Color* (*upper surface*).—137C.

*Size and shape.*—7.5 cm long, 4.5–5.0 cm wide, 5-lobed.

It is claimed:

1. A new and distinct cultivar of Chrysanthemum plant named Empire Scottsdale, as illustrated and described.

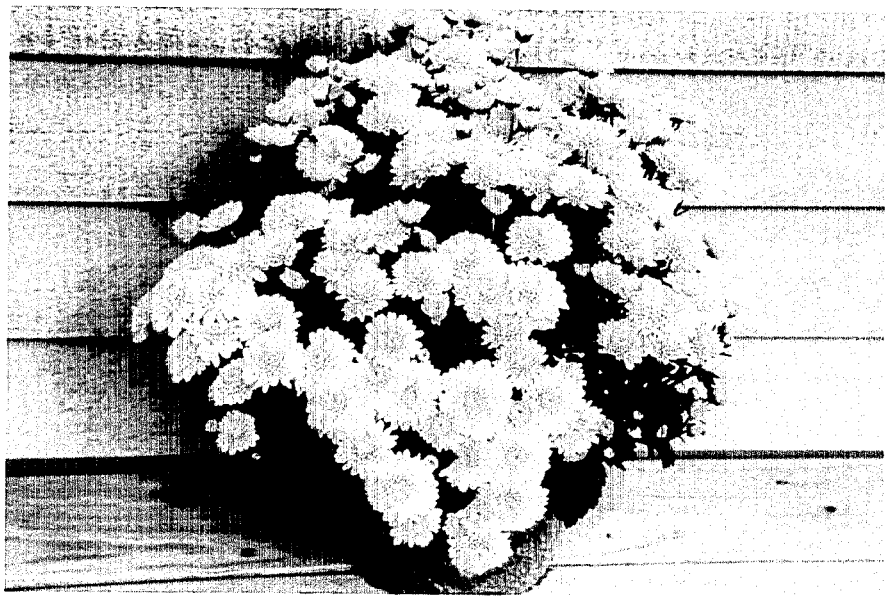

* * * * *